United States Patent [19]
Paschke et al.

[11] Patent Number: 5,395,240
[45] Date of Patent: Mar. 7, 1995

[54] STERILIZABLE DENTAL MEDICAL HANDPIECE CONTAINING ELECTRIC COIL

[75] Inventors: Richard H. Paschke, Medford; Marty I. Septimus, Forest Hills; George E. Warrin, North Merrick; Michael P. Parr, Northport, all of N.Y.

[73] Assignee: Dentsply Research & Development Corp., Milford, Del.

[21] Appl. No.: 120,900

[22] Filed: Sep. 14, 1993

[51] Int. Cl.⁶ ............................................. A61C 1/07
[52] U.S. Cl. ..................................... 433/119; 433/86
[58] Field of Search .............. 433/86, 119; 128/62 A, 128/24 AA; 607/97; 604/22; 310/340

[56] References Cited
U.S. PATENT DOCUMENTS

| | | | |
|---|---|---|---|
| Re. 30,536 | 3/1981 | Perdreaux, Jr. ............... | 433/86 |
| 1,043,683 | 11/1912 | Fieser . | |
| 3,375,583 | 7/1968 | Blank et al. ................... | 433/86 |
| 3,394,954 | 7/1968 | Sarns . | |
| 3,589,363 | 6/1971 | Banko et al. ................... | 604/22 |
| 3,603,621 | 9/1971 | Parsons ......................... | 285/174 |
| 3,654,502 | 4/1972 | Carmons et al. . | |
| 3,801,029 | 4/1974 | Malburg ........................ | 242/7.03 |
| 3,882,638 | 5/1975 | Black . | |
| 3,972,123 | 8/1976 | Black . | |
| 4,110,908 | 9/1978 | Cranston ....................... | 433/125 |
| 4,303,392 | 12/1981 | Rollofson ...................... | 433/126 |
| 4,333,197 | 6/1982 | Kuris ............................ | 433/119 |
| 4,399,703 | 8/1983 | Matzuk ......................... | 73/621 |
| 4,403,959 | 9/1983 | Hatakeyama ................. | 433/126 |
| 4,406,284 | 9/1983 | Banko ........................... | 433/86 |
| 4,412,402 | 11/1983 | Gallant ......................... | 433/88 |
| 4,428,748 | 1/1984 | Peyman et al. ............... | 604/22 |
| 4,492,574 | 1/1985 | Warrin et al. ................. | 433/81 |
| 4,534,734 | 8/1985 | Lares ............................ | 433/126 |
| 4,578,033 | 3/1986 | Mossle et al. ................. | 433/29 |
| 4,589,847 | 5/1986 | Loge et al. .................... | 433/126 |
| 4,741,731 | 5/1988 | Starck et al. .................. | 604/22 |
| 4,820,152 | 4/1989 | Warrin et al. ................. | 433/86 |
| 5,267,954 | 12/1993 | Nita .............................. | 128/24 AA |

OTHER PUBLICATIONS

Article for Parkell Handpiece, 1 page.
Article for Dentsply ®/Cavitron ® Model 3000 Ultrasonic Scaler 1 page.
Article for EMS Piezon ® Master 400 Handpiece 1 page.
Amadent's Neosonic-S ™ Peza-Utrasonic Scaler 2 pages.
Satelec ® Classic System Ultrasonic Scaler 2 pages.
Wisse Dental GmbH-Das Optison Handstuck-System 1 page.

*Primary Examiner*—Cary E. O'Connor
*Attorney, Agent, or Firm*—James B. Bieber; Edward J. Hanson, Jr.

[57] ABSTRACT

An ultrasonic handpiece wherein the entire assembled handpiece may be sterilized with an ingress of the sterilizing fluid into the interior of the handpiece. The handpiece is formed with an elongated housing sleeve and a coil unit for establishing an alternating magnetic field located therein. The housing sleeve and coil unit is assembled such that crevices are formed between the ends of the housing sleeve and coil unit, thus allowing steam, chemicals and heat to pass in and out of the interior of the handpiece for more rapid and thorough sterilizing of the handpiece. Further, the coil unit is not potted to the housing sleeve in order to allow for different thermal coefficients of expansion between materials without the buildup of undue stress.

32 Claims, 3 Drawing Sheets

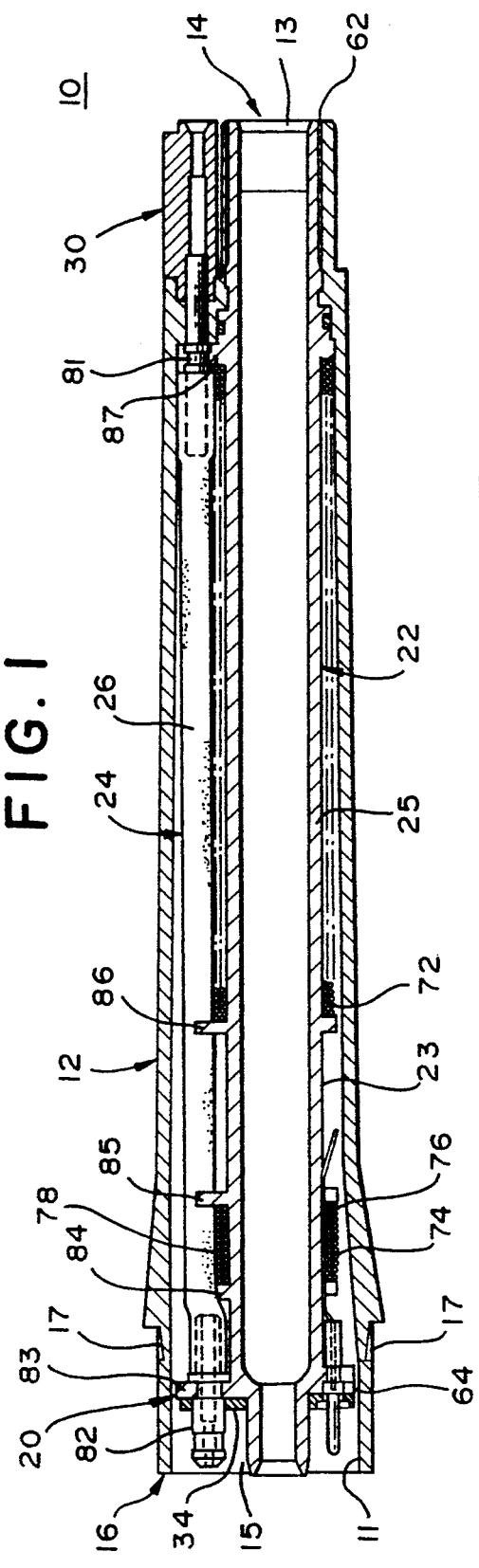
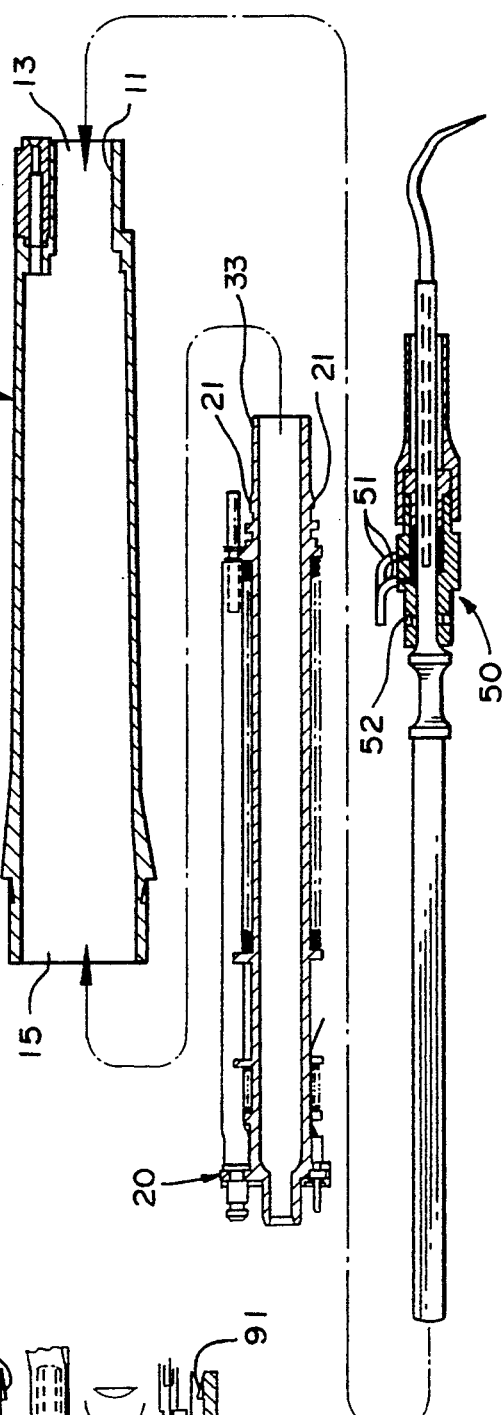
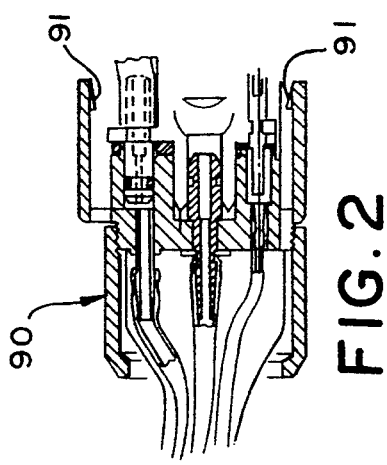

STERILIZABLE DENTAL MEDICAL HANDPIECE CONTAINING ELECTRIC COIL

BACKGROUND OF THE INVENTION

1. Field of the Invention

The present invention relates to handpieces containing an interior electrical winding, which handpieces are for use in treating mammals. More particularly the present invention relates in a preferred embodiment to ultrasonic dental/medical hand tools and more especially to an ultrasonic dental handpiece which can withstand the rigors of hundreds of cycles of sterilization using anyone of a number of currently widely used sterilization methods and equipment including autoclaving, dry heat at 190° C. and Chemical, while fully assembled without unacceptable detrimental effects to the handpiece. Specifically, the electrical components of the handpiece can be subjected to any of these sterilization techniques without material damage with fluid and heat entering the interior of the handpiece.

2. Description of the Prior Art

Ultrasonic dental handpieces employed during dental procedures for cutting or cleaning are well known.

One such example is U.S. Pat. No. 4,492,574 to Warrin et al., which teaches an ultrasonic endodontic dental handpiece having a coil for establishing an alternating magnetic field, the housing having a cooling fluid inlet at one end and being open at the other end for receiving and supporting a removable insert.

Today, cross contamination has become a major concern in the medical and dental fields. Bacteria and viruses from one patient's mouth can be transferred to another patient if the handpiece is not adequately sterilized. Therefore, sterilization of dental instruments has become almost mandatory. However, due to the sensitive nature of the electrical and mechanical components involved with ultrasonic handpieces, sterilization of the entire handpiece was previously limited.

Prior to this invention the more usual method used to cleanse and disinfect ultrasonic handpieces was to wipe the exterior of the handpiece using a disinfecting solution. Where autoclaving was alleged to be acceptable, its use was limited to handpieces of simpler design having only heavy gauge wire windings.

In many prior art handpieces a coil of conductive wire within the handpiece was connected permanently by a cable to a power source. An oscillating current within the coil in the handpiece produced a magnetic field to induce motion within a magnetostrictive element separable and removably inserted within the magnetic field within the handpiece. The magnetostrictive element was connected by a metal body to a dental tool which was caused to vibrate at ultrasonic speeds to clean and reduce teeth, calculus, cartilage and bone. High temperature and steam sterilization methods were not suitable for sterilizing these handpieces because they would cause short-circuiting in the coils and connections and degradation of mechanical parts, resulting in impractically short useful life.

The present invention has overcome the problems encountered in the art by providing an ultrasonic handpiece which is removed from the cable and effectively sterilized without the need for further disassembly by one of several methods available, including autoclave and other steam sterilization techniques, high temperature dry sterilization, Chemiclave®, and using other liquid sterilants at room and elevated temperatures. The invention is broadly applicable to dental/medical handpieces of diverse uses including handpieces such as for dental scalers, medical scalers, endodontic, orthopedic and nasal medical handpieces and combinations thereof. The preferred embodiment of the invention is in dental handpieces.

While described in detail in its most preferred embodiment of a dental handpiece the present invention is directly applicable to other dental, medical and veterinary tools having electric coils proximate to a patient so that superior sterilization is indicated by good dental, medical or veterinary practice.

SUMMARY OF THE INVENTION

The present invention in a preferred embodiment provides an ultrasonic handpiece which can be sterilized by anyone of a number of current methods when fully assembled without excessive detrimental effects to any of the handpiece components. The handpiece has been specifically constructed in a preferred embodiment to include a housing member or sleeve and a coil unit, which when assembled, are loose fitting at the anterior end of the coil unit, thereby allowing sterilizing fluids such as steam, chemicals and/or heat to enter the interior of the handpiece for more rapid and thorough sterilization of the entire handpiece. By loose fitting it is not meant to connotate how difficult it might be to disassemble the handpiece, but rather that there is an opening or crevice and preferably at least two, and more preferable, more than two openings or crevices extending into the interior of the handpiece and especially the coil winding area or space.

The inner wall of the housing and outer periphery of the coil unit at the anterior end and posterior end are dimensioned such that when assembled together, they frictionally lock together, but allow crevices to exist therebetween. This frictional lock is not intended for disassembly during cleaning but is basically a permanent frictional lock intended to hold for the life of the handpiece. The handpiece interior coil area thus must be sterilized without disassembly.

Still further, the handpiece has been constructed so as in its preferred form to require no potting, thus the electrical windings which in a preferred form are copper wire, including a thin gauge feedback wire winding, and the plastic housing sheath and coil form of dissimilar coefficients of expansion may go through the necessary changes in dimension during heating and cooling cycle processing without being destroyed or highly deleteriously affected from the buildup of stresses.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a fragmentary longitudinal sectional view of the assembled handpiece.

FIG. 2 is a sectional view of a quick connect and disconnect cable assembly.

FIG. 3 is an exploded view showing the assembly of the handpiece.

DESCRIPTION OF THE PREFERRED EMBODIMENTS

Figure 4:
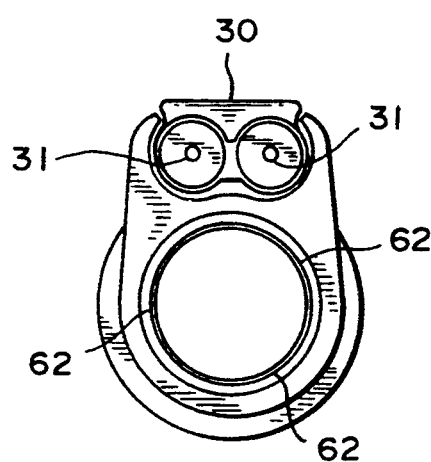
FIG. 4 is a front end view illustrating the crevices.

Several variant detailed embodiments of the present invention are disclosed herein, however, it is to be understood that the disclosed embodiments are merely exemplary of the invention, which may be embodied in various forms.

Turning to the drawings, an assembled ultrasonic dental handpiece 10 in accordance with the invention is shown in FIG. 1. Handpiece 10 includes an outer, tubular handpiece housing 12 which has an open interior and is open at both ends and in a preferred embodiment has an outer dimension surface that is continuous without crevices penetrating to the interior of the housing. In a preferred embodiment the outer surface of the housing is substantially cylindrical. The front end 14 of the housing includes an opening 13 which is smaller in diameter than opening 15 in the rear end 16. The rear end 16 is configured so it may be conveniently separated from an external cable assembly 90, shown in FIG. 2, which provides power and a fluid inlet and outlet to the handpiece. Cable assembly 90 slides onto and off of the housing 12 and is held in connected position by tabs 91 which cooperate to engage grooves 17 when the end of the cable assembly 90 is engaged. At the front end 14 of handpiece 10 is a separately molded sterilizable elastomeric receptacle nozzle 30 into which the fluid supply stems 51 of various tools 50 may be inserted.

Housing 12 in preferred embodiments is made from a plastic material that will withstand all of the sterilization conditions set forth below—dry heat at 190° C., steam autoclaving and chemical, for the number of cycles established as standards for preferred embodiments. A polyether-imide or a glass fiber reinforced, amorphous polyamide resin, Grivory Superstiff, a product of EMS—American Grilon Inc., 2060 Corporate Way, Sumter, S.C. 29151 and a Liquid Crystal Polymer material, Vectra A530, a product of Hoechst-Celanese, 26 Main Street, Chathim, N.J. 07928 have been found to be acceptable materials.

Figure 5:
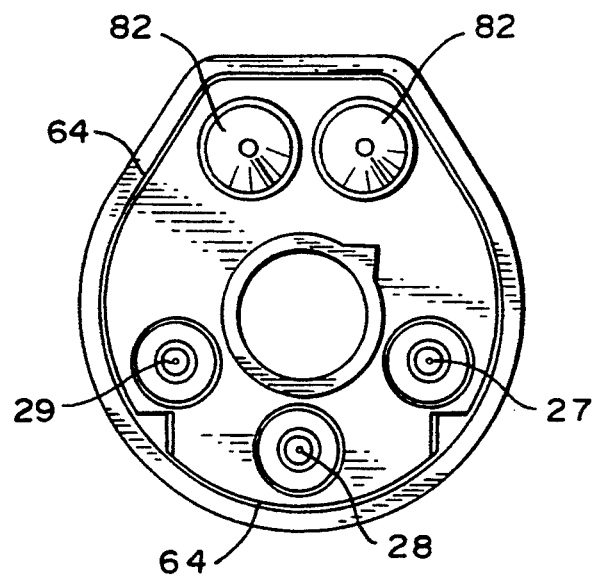
FIG. 5 is a rear end view illustrating the crevices.

A coil and tube assembly 20 are inserted within housing 12. The assembly 20 includes a coil unit 22, fluid conducting units 24 and pin positioner 34. Each of the fluid conducting units 24 includes a tube 26 which in a preferred embodiment is manufactured from silicone rubber and stainless steel hose coupling pins 81 and 82 at the tube's front and rear ends, respectively. The pin positioner 34 snaps onto the coil unit 22 and accurately aligns three electrical pins 27, 28, 29 (FIG. 5) with respect to the central water tube in order to insure proper engagement with mating sockets in the cable assembly 90. The front coupling pins 81 cooperate with the molded receptacle 30, and the rear coupling pins 82 cooperate with the external cable assembly 90. The tubes 26 and pins 81 and 82 are supported on the coil unit 22 by a plurality of spaced flanges 83–87 located on the coil form 25.

The tubes 26 are part of a fluid dispensing system used in combination with the ultrasonic instrument embodiment illustrated in FIGS. 1-5. The fluid dispensing system enables a controlled selective delivery of an irrigating fluid longitudinally of the handpiece. Methods of supplying fluids to a handpiece and methods of using ultrasonic endodontic handpieces are disclosed in U.S. Pat. No. 4,820,152 and the references cited therein, which are all hereby incorporated by reference.

Coil unit 22 includes drive coil 72, which is connectable to an alternating current source. Drive coil 72 is wound in a double coil between flanges 86 and 87, and provides an alternating electromagnetic field in handpiece 10.

Feedback coil 76 is a fine wire and is provided to register voltage developed by the movement of, for example, an ultrasonic scaler insert 50 in the electromagnetic field of handpiece 10. Feedback coil 76 is wound in five layers starting on a polytetrafluoroethylene tape which is directly against the coil form 25 between flanges 84 and 85 and is connected to ground terminal 28 and terminal 29. The preferred gauge of the fine wire is 45–30 (AWG). Bucking coil 74 is heavier wire than the feedback coil 76 and is wound in one layer over the feedback coil. The bucking coil 74 is provided to minimize transformer coupling between drive coil 72 and feedback coil 76. Bucking coil 74 and drive coil 72 are connected between terminals 27 and 28 in one continuous wire. Drive coil 72 is attached to terminal 27 and using a right hand turn, for example, is wound from flange 86 to flange 87 and back. The wire from drive coil 72 then traverses space 23 between flanges 85 and 86, and using a left hand turn, is wound between flanges 84 and 85 to produce bucking coil 74. The end of the wire is then connected to terminal 28. Bucking coil 74 and drive coil 72 are wired in series and are wound in opposite directions and are therefore electromagnetically 180° out of phase. The bucking coil is electrically insulated from the feedback coil. Wires connected to terminals 27 and 29 provide the power source and register feedback, and a wire connected to terminal 28 acts as a common ground.

Interposed preferably between all winding layers of the feedback coil 76 and the bucking coil 74 is a layer of polytetrafluoroethylene tape 78. In another embodiment polytetrafluoroethylene tape is also used between the layers of drive coil 72. In an alternative embodiment, the wire from which the coils are formed is coated preferably with polytetrafluoroethylene and in a preferred embodiment the wire is copper wire coated with polytetrafluoroethylene and the tape is omitted. The polytetrafluoroethylene is used to improve the interlayer insulation between the coils, which prolongs the life and the number of autoclaving cycles the handpiece can withstand without shorting between layers.

A polytetrafluoroethylene tape is Allied Signal Fluorglas PTFE T-100 virgin skived film 0.002 inches thick. The tape should exhibit conformability, be chemically inert, be nonporous, and withstand a continuous operatory temperature range of 0° C. to +205° C.

The tape is particularly important with conventional copper wire having polyester and/or polyamide-imide insulation on it, such as Polyflex 220 (Elektrisola).

The drive coil and bucking coil may be made of 22 gauge wire such as Polyflex 220.

The feedback coil may be made of 38 gauge wire such as Polyflex 220.

Preferred copper wire is polytetrafluoroethylene coated, preferably TFE polytetrafluoroethylene with 0.0007 to 0.0011 inch thick insulation on the 38 gauge wire and 0.0020 to 0.0029 inch thick insulation on the 22 gauge wire (Phoenix Wire). The teflon coating should exhibit chemical inertness, high and low temperature stability, excellent electrical properties and good adhesion to the copper conductors.

With reference to FIG. 3, the assembly of the ultrasonic dispensing hand tool will be set forth. First, coil and tube assembly 20 is inserted into the housing 12 from the larger diameter opening 15 and forced forward such that ribs 21, molded on the exterior of substantially cylindrical coil form 25, engage the interior wall 11 of the housing 12 to frictionally lock the coil and tube assembly 20 in place. Thereafter, instrument 50 is inserted through the front opening 13 until fluid supply and return stems 51 are seated in apertures 31 in nozzle 30. O-ring 52 on instrument 50 prevents cooling fluid flowing into the center of coil form 25 from passing therebeyond. Once the handpiece 10 is assembled, cable assembly 90 can be coupled to the rear end 16 thereof.

The tolerances of the housing 12 and coil form 25 are such that a crevice or clearance space 62 (FIG. 4) is formed between the interior wall 11 of the housing 12 and outer wall 33 of coil form 25 at front end 14. At rear end 16, a crevice or clearance space 64 (FIG. 5) exists between the outer periphery of flange 83 and inner wall 11. The crevices 62 and 64 have been exaggerated in the front end view shown in FIG. 4 and the rear end view shown in FIG. 5. A crevice opening of 0.25 mm high has been found to give good performance. A preferred crevice opening range is 0.01 to 0.5, more preferably 0.02 to 0.35 mm in dimension. In preferred embodiments at least two separate crevice openings are provided and in a still more preferred embodiment three or more crevice openings are provided. The preferred crevice will admit the sterilizing fluid to enable sterilization within the conventional time periods used for sterilization. The preferred crevice will limit the entrance into the interior of the handpiece of debris that would interfere with the electrical field or otherwise deleteriously affect handpiece sterilization or performance.

The handpiece 10 can also be manufactured such that crevices exist only at one end of the assembly. In a preferred embodiment crevices would be present only at the rear of the handpiece remote from the working end to resist fluid and other material present in the dental patients oral cavity from entering into the anterior of the handpiece housing. The crevices are formed by ribs 21 or by a loose abutting fit between the parts. Coil form 25, which includes ribs 21 and flanges 83–87 is preferably manufactured from the same material as housing 12. By using the same materials, the coefficients of expansion will be the same. Therefore, the stresses between the elements which are frictionally locked together will remain the same during heating and cooling. In some instances, materials having different coefficients of expansion will be preferred. The crevices between the ends of the coil unit and the ends of the housing provide sterilization passageways or openings allowing fluid and heat into the interior of handpiece 10 in order to sterilize the inner workings of the handpiece.

For preferred embodiments of the invention the handpiece must stand up to repetitious cycling at dry heat temperatures of 190° C. with long and short cycle times which stress material, to steam autoclaving which subjects materials to moisture at 134° C., to chemical vapor sterilization using formaldehyde/alcohol chemicals at 132° C. The plastics from which the coil form 25 and housing 12 are preferable formed, must not fracture, craze or distort under any of these conditions so the device will have wide application in the dental/medical field. The tape and/or coating on the windings must not break down and lose insulation characteristics and permit materially detrimental shorting. Shorting between overlapping coils is particularly damaging to the continued effective operation of the handpiece. Of special concern with maintaining electrical integrity is the fine wire winding of the feedback coil 76. This wire is more sensitive to shorting under conditions of moisture and/or high temperature sterilization.

Figure 6:
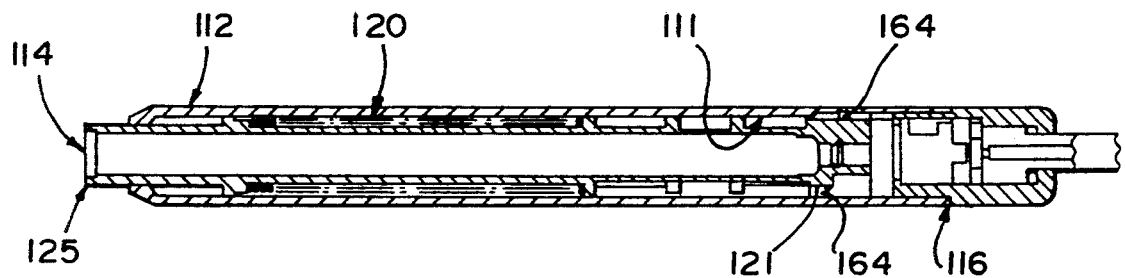
FIG. 6 is a fragmentary longitudinal sectional view of a second embodiment.
Figure 7:
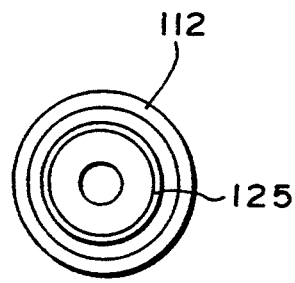
FIG. 7 is a front end view of the embodiment shown in FIG. 6.
Figure 8:
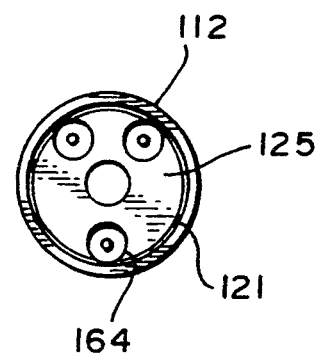
FIG. 8 is a rear end view of the embodiment shown in FIG. 6.

FIGS. 6–8 illustrate an alternative embodiment which does not include fluid conducting units 24. This embodiment includes a housing 112 and a coil assembly 120, which when assembled, creates crevices 164 at the rear end 116. The outer circumference of the coil form 125, proximate the rear end 116, includes a rib 121 molded therewith. The rib 121 mates with the inner wall 111 of housing 112 such that crevices 164 are formed when connecting the coil unit to the housing. The outer circumference of the coil form 125 proximate front end 114 engages inner wall 111 to snaplock and frictionally lock coil form 125 to housing 112. The outer diameter of the coil form 125 has a slightly raised rim and the inner diameter of the housing 112 has a slight circumferential groove into which the rim snaps.

Figure 9:
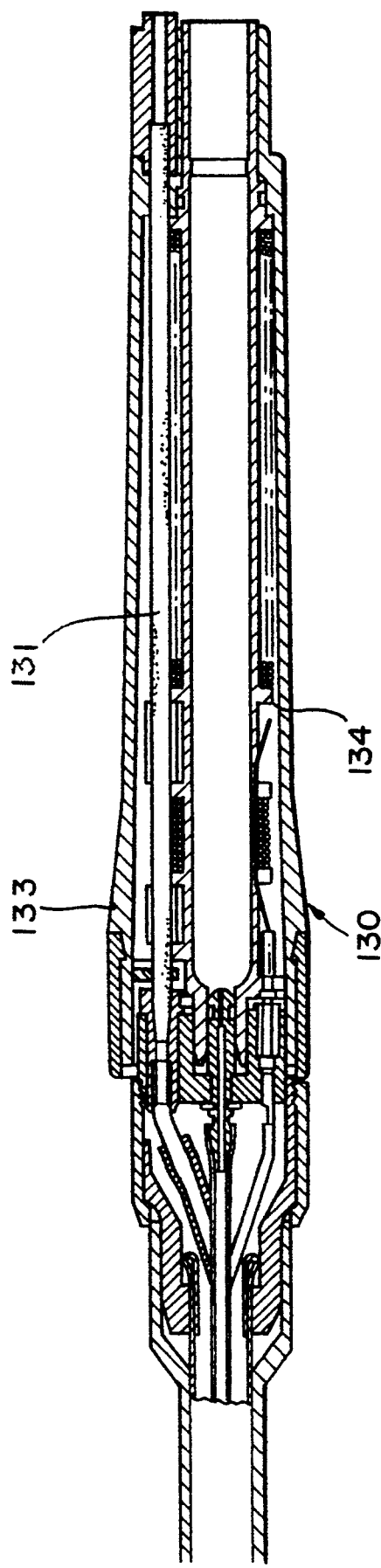
FIG. 9 is a fragmentary longitudinal sectional view of a third embodiment.
Figure 10:
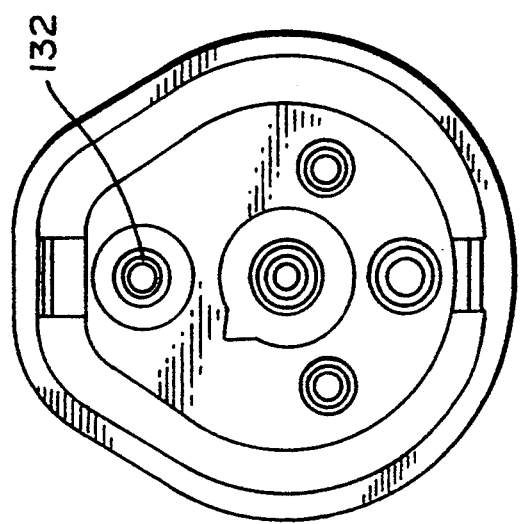
FIG. 10 is a sectional view of a quick connect and disconnect cable assembly for the third embodiment.

FIGS. 9 and 10 illustrate another alternative embodiment 130 which includes a single fluid carrying and dispensing tube 131 which connects to a source of air conveying powder as taught by U.S. Pat. Nos. 4,820,152 and 4,412,402 which are hereby incorporated by reference. Indeed the handpiece is a multifunction handpiece as described in U.S. Pat. No. 4,820,152. This embodiment includes a housing sleeve 133 and a coil assembly 134, which are molded to assemble in the same manner as the first described embodiment 10 of FIGS. 1–5. The electrical connections and windings are as shown in FIGS. 1–5, the primary difference being as described above respecting the fluid carrying tube arrangement which is a single stainless steel hypodermic tube.

A preferred method of sterilizing a preferred ultrasonic dental or medical handpiece made according to the present invention involves placing the handpiece in an autoclave. Exemplary autoclaves are:

Steam Autoclaves

Pelton & Crane Validator Plus 10
    Operating: Temp. 134° C. (273° F.); Time Wrapped—12 mins. Unwrapped—3 mins.
    Cooling/Drying Time: 20 minutes Tuttnauer Model 2540M
    Operating: Temp. 134° C. (273° F.); Time Wrapped—13 mins. Unwrapped—3 mins.
    Cooling/Drying Time: 15 minutes Statim Cassette Autoclave
    Operating: Temp. 134° C. (273° F.); Time Wrapped—10 mins. Unwrapped—3 mins.
    Cooling/Drying Time: 10 minutes Chemical Vapor MDT Chemiclave Model 5000
    Operating: Temp. 132° C. (270° F.); Time—20 mins.
    Cooling/Drying Time: 10 minutes

Rapid Dry heat

Cox Transfer Sterilizer
  Operating: Temp 190° C.; Time Wrapped—12 mins.
    Unwrapped—6 mins.
  Cooling Time: 20 minutes

Dry Heat

Columbus Dental Dri-Clave Model 75
  Operating: Temp 160° C.; Time—30 mins.
  Cooling Time: 10 minutes It is a usual and preferred practice to ultrasonicly clean the preferred ultrasonic dental or medical handpieces before placing them in an autoclave or other sterilizer. Exemplary ultrasonic cleaners are:

Ultrasonic Cleaners

L&R Cleaning System Model 2014
L&R Quantrex cleaner Model 140

Twenty-two ultrasonic handpieces constructed as shown in FIGS. 6–8 were sterilized to test the effectiveness of this preferred embodiment of the invention. Different handpieces or groups of handpieces were placed in each of the sterilizers listed above. The sterilizers were operated according to their instructions and as indicated above. All handpieces were subjected to a cleaning cycle in an ultrasonic bath prior to being placed in the various sterilizing equipment as is the routine recommended procedure. Achievement of sterility of the handpieces was determined by an independent biological laboratory, Luizzi Microbiology Lab. The procedures followed were those selected from the USP XXII and the text ANTISEPTICS, DISINFECTANTS, FUNGICIDES AND STERILIZATION edited by copyright 1954. G. F. Reddish, chapter 7, page 142 METHODS OF TESTING CHEMICAL STERILIZERS AND TESTING FOR STERILITY, published by Lea & Febiger, Philadelphia which has been used generally as the sterilization handbook since 1954.

The cleaning—sterilization cycle consisted of immersing the handpiece in a non-ionic cleaning solution and operating the ultrasonic cleaning unit for a period of five (5) minutes. The handpiece was removed from the cleaning unit and dried and either wrapped in a sterilizer pouch and sealed or placed on the tray unwrapped in the various sterilizers. The handpieces were then sterilized. Afterwards they were sent to the biological laboratory and contaminated according to the following protocol. They were immersed in a mixed culture broth consisting of Bacillus Subtilis ATCC #9372 and Bacillus Stearothermophilus ATCC #7953. Then the handpieces were returned and recleaned and sterilized as previously described. The handpieces were then returned to the biological laboratory and placed in media broth, and incubated at required temperatures for seven (7) days and found to have a total kill and be sterile.

It should be understood that the steam and other sterilizing mediums had ingressed into the breach or crevices in the handpiece into the open area inside the handpiece occupied by the electrically conductive coil.

Five preferred handpieces of the type described respecting the sterilization testing were subjected to the same procedure of sterilization described for steam autoclaving for 700 cycles. This included the ultrasonic cleaning procedure. Two (2) were tested with the Validator (1) in the wrapped condition and (1) in the unwrapped condition; (1) with the Tuttnauer in the unwrapped condition; and the balance with the Statim (1) wrapped and (1) unwrapped. One wrapped handpiece failed after 450 cycles in the Statim. A second wrapped handpiece failed after 650 cycles in the Validator. From this a test is drawn. The test is that in at least one out of three repetitions of 20 handpieces chosen at random, at least 95% of the handpieces will survive 400 steam sterilizing cycles, with each cycle being at a temperature of at least 134° C. for at least 12 minutes.

Twelve (12) preferred handpieces of the type described respecting the sterilization testing were subjected to the same procedure described for dry air sterilization for 800 cycles. This included the ultrasonic cleaning procedure. Six (6) were tested with the Columbus Dental Dri-Clave model 75, (3) in the wrapped and (3) in the unwrapped condition. One wrapped handpiece failed after 600 cycles. A second wrapped handpiece failed after 750 cycles. Six (6) were tested in the Cox Transfer Sterilizer (3) in the wrapped condition and (3) in the unwrapped condition. One (1) wrapped handpiece failed after 650 cycles, (2) wrapped handpieces failed after 700 cycles and (2) unwrapped handpieces failed after 750 cycles. From this a test is drawn. The test is that in at least one out of three repetitious of 20 handpieces chosen at random, at least 95% of the handpieces will survive 400 sterilizing cycles of dry heat at 190° C. with each cycle being either the rapid dry heat or the regular dry heat method as described above.

Failure was determined by failing anyone of the following criteria: no cracks or crazing were present, no water leaks appeared from the cooling water system or treatment water or fluid system, less than 10% degradation in the power or mechanical output as monitored by a Clark-Hess ultrasonic power meter and Nikon Optical Comparator respectively, oscillation did not cease when handpiece activated, housing and coil form do not deform such that insert will no longer seat properly and/or connection will no longer mate properly. The handpieces were retested at the end of each 50 cycles.

When the generic term "universal-sterilizable" or "universal-sterilized" handpiece or material is used in this patent application it is meant that the handpiece will pass the biological sterility test set forth above, the autoclave test set forth above and both of the high temperature (190° C.) test set forth above and withstand a useful number of chemical sterilization cycles as set forth above.

The assembly of the housing and the coil unit of the present invention in its preferred forms has no potting, thereby facilitating steam, chemicals and/or heat to pass into and out of the interior chamber formed between the housing and the coil assembly. Having a coil assembly free of potting also allows for the heating and cooling expansion and contraction of parts of different coefficients of expansion without the coil wire developing electrical short circuits. The elimination of potting is particularly challenging respecting the thin gauge wire which is especially subject to many damaging influences. The novel method of assembly uses both a snaplock and friction to lock together components of similar or dissimilar coefficients of expansion and intentionally creates crevices between these components to allow for autoclaving of the interior and exterior of an assembled handpiece. This provides efficient and thorough sterilization of the entire handpiece.

It will be understood that "handpiece" as used in this patent application refers to a device suitable for holding in the human hand of a professional such as in the preferred form of this invention, a dentist or a dental hygienist, for hand manipulation in carrying out a treatment procedure in a dental operatory. A particularly important feature of the invention, in its most preferred present use, is providing for autoclavable sterility of interior areas of the handpiece where the electrical winding is housed regardless of any seepage around fittings, electrical, fluid or instrument mounting or the like or at other joining of parts. It may be seen that this is done by providing openings or crevices to the interior open space within the interior of the housing of the handpiece and directly exposing the coil. The coil wire is of course coated or insulated from shorting, while being free of potting and without rigid securement, so that the expansion and contraction inherent in autoclave cycling will not result in reducing the useful life of the handpiece in an uneconomical degree.

While various preferred embodiments have been shown and described, it will be understood that there is no intent to limit the invention by such disclosure, but rather, it is intended to cover all modifications and alternate constructions falling within the spirit and scope of the invention as defined in the appended claims.

We claim:

1. An ultrasonic handpiece comprising:
    an elongated housing sleeve made from universal-sterilizable material and comprising an inner wall;
    a coil unit made from universal-sterilizable material and comprising at least one coil and having an outer dimension proximate one end which is configured to abut said inner wall of said housing sleeve when assembled within said housing sleeve such that at least one crevice exist therebetween and opening to said coil; and
    wherein the coil unit is assembled within the housing sleeve such that the entire assembly can be repetitiously universally-sterilized with the passage of universal-sterilizing fluids through said crevice into said elongated housing sleeve and to said coil.

2. The handpiece of claim 1 wherein a portion proximate an end opposite said one end of said coil unit includes an outer dimension which is configured to frictionally engage said inner wall to provide securement of said coil unit within said housing.

3. The handpiece of claim 2 wherein said end opposite said one end has an outer circumferential configuration in which at least three crevices exist between the outer circumference of said coil unit and said inner wall of said housing.

4. The handpiece of claim 2 wherein the outer dimension surface of the coil unit which engages said inner wall of said housing is made from a material having the same coefficient of expansion as said housing.

5. The handpiece of claim 1 wherein the outer dimension of said coil unit proximate either said one end or the end opposite said one end includes ribs which frictionally lock the coil unit within said housing while leaving at least two crevices between said inner wall and said outer dimension.

6. An ultrasonic handpiece comprising:
    a hollow housing sleeve having an inner wall extending from a first end to a second end;
    a coil adapted to be connected to an external energy source for establishing an alternating electromagnetic field within said housing, said coil having a coil form about which wire coil is wrapped;
    said coil assembled within said housing sleeve such that crevices are formed between said inner wall and said coil form proximate one of said first or second ends; and,
    wherein the handpiece is autoclavable when assembled and said crevices allow for fluid flow into and out of the interior of the handpiece, resulting in more rapid heating and efficient cleaning.

7. The handpiece of claim 6 wherein crevices are formed at both said first and second ends.

8. The handpiece of claim 6 wherein said coil form and said housing are made from a material having the same coefficient of expansion.

9. The handpiece of claim 6 wherein said coil form includes portions which are secured to said housing by friction.

10. The handpiece of claim 9 wherein said portions are in the form of ribs molded with the coil form.

11. The handpiece of claim 6 wherein said coil includes at least two wire coil layers of a feedback coil having a wire gauge smaller than 30 (AWG) and an insulating sheet interposed between said two coil layers of said feedback coil.

12. The handpiece of claim 11 wherein said insulating sheet comprises a non woven polytetrafluoroethylene film.

13. The handpiece of claim 6 wherein said coil includes at least two wire coil layers of a drive coil and an insulating sheet interposed between said two coil layer of said drive coil.

14. The handpiece of claim 6 wherein said handpiece is universally-sterilizable and said coil includes a wire feedback coil and said handpiece comprising a wire drive coil and said wires are coated with an insulation.

15. The handpiece of claim 14 wherein said wire insulation consisting essentially of polytetrafluoroethylene.

16. The handpiece of claim 6 further comprising at least one fluid dispensing tube for delivering and dispensing a fluid.

17. A method of making an ultrasonic handpiece comprising:
    a) forming a hollow housing sleeve with first and second ends;
    b) assembling a coil unit free of potting and having first and second ends corresponding to the first and second ends of said housing sleeve, said coil unit when connected to an external source creating an alternating magnetic field; and,
    c) frictionally securing said coil unit within said hollow housing sleeve such that crevices exist at least at one respective corresponding end thereof between a corresponding end of said sleeve and said coil unit.

18. A sterilizable electrical winding activated handpiece for use in treating mammals comprising a handpiece housing having an interior enclosing an electrical winding, said housing having at least one sterilizing medium admitting opening into its interior extending to said electrical winding, wherein the winding comprises a coil of coated wire that is not potted but insulated such that said winding is capable of repeated sterilizations without failure.

19. The handpiece of claim 18 wherein said opening into the interior of said housing opens to and around said electrical winding when said handpiece is exposed to an intended sterilizing medium.

20. The handpiece of claim 18 wherein the winding comprising a coil of coated wire that is not potted and said housing member having an open interior and at least one winding of said coated wire of said coil is directly exposed to said open interior of said housing member.

21. The handpiece of claim 18 comprising at least one coil being formed using a high temperature, non-porous polytetrafluoroethylene coated wire.

22. The handpiece of claim 21 wherein said handpiece is a dental handpiece and said coil comprising fine gauge wire and said fine gauge wire coil is not potted.

23. The handpiece of claim 22 wherein said fine gauge wire is a feedback coil and said handpiece comprising bucking and drive coils and at least one layer of polytetrafluoroethylene tape interposed between all coil layers of said feedback coil and all three of said coils comprising copper wire.

24. A sterilizable electrical winding activated handpiece for use in treating mammals comprising a handpiece housing having an interior enclosing an electrical winding, said housing having at least one sterilizing medium admitting opening into its interior extending to said electrical winding, the winding comprising a coil of coated wire that is not potted and said housing member having an open interior and at least one winding of said coated wire coil directly exposed to said open interior of said housing member, wherein the winding is on a coil form and the housing member and the coil form comprising material having the same coefficient of expansion and contraction during heating and cooling sterilization cycling.

25. The handpiece of claim 24 wherein the coil form is connected to the housing member solely through frictional engagement.

26. A sterilizable electrical winding activated handpiece for use in treating mammals comprising a handpiece housing having an interior enclosing an electrical winding, said housing having at least one sterilizing medium admitting opening into its interior extending to said electrical winding, the winding comprising a coil of coated wire that is not potted and said housing member having an open interior and at least one winding of said coated wire coil directly exposed to said open interior of said housing member, wherein the winding is on a coil form and the housing member and the coil form comprising material having different coefficients of expansion and contraction during heating and cooling sterilization cycling.

27. An autoclavable ultrasonic dental or medical handpiece for use in dentistry or medicine comprising an assembly comprising an elongated housing sleeve and a conductive coil unit, said assembly including a breach or opening for autoclaving by steam, said opening providing for the rapid diffusion and penetration within the assembly and removal therefrom of steam, said coil unit comprising an insulated wire winding that is not potted, said winding capable of repeated autoclaving without electrical and mechanical failure.

28. The handpiece of claim 27, wherein said handpiece is selected from the group consisting of a dental scaler, medical scaler, an endodontic instrument, orthopedic instrument, nasal medical instrument, and a combination thereof.

29. An autoclavable ultrasonic dental or medical handpiece for use in dentistry or medicine comprising an assembly comprising an elongated housing sleeve and a conductive coil unit, said assembly including a breach or opening for autoclaving by steam, said opening providing for the rapid diffusion and penetration within the assembly and removal therefrom of steam, wherein said housing sleeve and conductive coil unit consist essentially of heat resistant and autoclavable material that will sustain 400 steam sterilizing cycles, each cycle being at a temperature of at least 134° C. for at least 12 minutes, at least 95% of the time in at least one out of three repetitions of twenty handpieces chosen at random.

30. An autoclavable ultrasonic dental or medical handpiece for use in dentistry or medicine as a dental scaler, medical scaler, or an endodontic, orthopedic, or nasal medical instrument or a combination thereof, comprising an assembly comprising an elongated housing sleeve and a conductive coil unit, said assembly including a breach or opening for autoclaving by steam, said opening providing for the rapid diffusion and penetration within the assembly and removal therefrom of steam, wherein said coil unit comprises a coil of fine wire having a smaller diameter than 30 gauge (AWG).

31. A method of autoclaving an ultrasonic dental or medical handpiece comprising an electrically conductive coil within an open space inside of said handpiece, said method comprising placing said handpiece in an autoclave and subjecting said handpiece to steam at a temperature of at least 134° C. for at least 10 minutes said steam ingressing into a breach, opening or crevice in said handpiece into the space occupied by said conductive coil.

32. The method of claim 31 wherein the handpiece comprising a housing sleeve and conductive coil unit consist essentially of heat resistant and autoclavable material that will sustain 400 steam autoclave sterilizing cycles at a temperature of at least 134° C. for at least 12 minutes, at least 95% of the time in at least one out of three repetitions of 20 handpieces chosen at random.

* * * * *